(12) United States Patent
Riihimäki

(10) Patent No.: US 7,726,956 B2
(45) Date of Patent: Jun. 1, 2010

(54) COMBINATION ASSEMBLY FOR MANAGING A HOSE OR LIKE ELASTIC PUMP TUBE IN A POSITIVE DISPLACEMENT PUMP

(75) Inventor: Matti Riihimäki, Lappeenranta (FI)

(73) Assignee: Larox Flowsys Oy, Lappeenranta (FI)

( * ) Notice: Subject to any disclaimer, the term of this patent is extended or adjusted under 35 U.S.C. 154(b) by 643 days.

(21) Appl. No.: 10/546,778

(22) PCT Filed: Feb. 27, 2004

(86) PCT No.: PCT/FI2004/000106

§ 371 (c)(1),
(2), (4) Date: Oct. 24, 2005

(87) PCT Pub. No.: WO2004/076861

PCT Pub. Date: Sep. 10, 2004

(65) Prior Publication Data

US 2006/0110275 A1    May 25, 2006

(30) Foreign Application Priority Data

Feb. 28, 2003    (FI)    ................................. 20030312

(51) Int. Cl.
F04B 43/12    (2006.01)
(52) U.S. Cl. ...................................... 417/476; 417/221
(58) Field of Classification Search ............. 417/477.1, 417/218, 221; 285/239, 242
See application file for complete search history.

(56) References Cited

U.S. PATENT DOCUMENTS

| | | | | |
|---|---|---|---|---|
| 1,845,479 A | | 2/1932 | Carpenter | |
| 2,251,235 A | * | 7/1941 | Weydell | 418/45 |
| 3,463,196 A | * | 8/1969 | Richardson | 138/96 R |
| 4,111,234 A | * | 9/1978 | Wells et al. | 138/99 |
| 4,150,848 A | * | 4/1979 | Dyrup | 285/238 |
| 4,423,753 A | * | 1/1984 | Smith et al. | 138/89 |
| 4,484,864 A | * | 11/1984 | Michel | 417/477.8 |
| 4,568,255 A | | 2/1986 | Lavender et al. | 417/477 |
| 4,740,012 A | * | 4/1988 | Kondo et al. | 280/124.144 |
| 4,830,589 A | * | 5/1989 | Pareja | 417/539 |
| 4,838,134 A | * | 6/1989 | Ruland | 81/467 |
| 5,076,057 A | * | 12/1991 | Maruno | 60/487 |
| 5,868,438 A | * | 2/1999 | Svetlik | 285/114 |

FOREIGN PATENT DOCUMENTS

| | | |
|---|---|---|
| EP | 0 496 379 B1 | 4/1995 |
| FR | 1114877 | 4/1956 |
| WO | 97/41353 A1 | 11/1997 |

OTHER PUBLICATIONS

Author: Nicholas P. Chironis, Title: "Mechanisms, Linkages, and Mechanical Controls", Imprint in 1995, Publisher: McGraw-Hill, Inc., p. 115, Figure 10 and caption titled "Worm Adjustment."*

* cited by examiner

Primary Examiner—Devon C Kramer
Assistant Examiner—Dnyanesh Kasture
(74) Attorney, Agent, or Firm—Kubovcik & Kubovcik

(57) ABSTRACT

A combination assembly is disclosed for managing a hose or like elastic pump tube or pump channel such that particularly is used in a peristaltic pump. The invention is characterized by having the pump equipped with an assembly for the adjustment of the pump pressure and/or compression imposed on the hose/tube, the assembly comprising a steplessly adjustable eccentric adjustment mechanism.

13 Claims, 8 Drawing Sheets

A - A

COMBINATION ASSEMBLY FOR MANAGING A HOSE OR LIKE ELASTIC PUMP TUBE IN A POSITIVE DISPLACEMENT PUMP

This application is a 371 of international application PCT/FI2004/000106, which claims priority based on Finnish patent application No. 20030312, filed Feb. 28, 2003, which is incorporated herein by reference.

The present invention relates to a combination assembly according to the preamble of claim 1 for managing a hose or like elastic pump tube or pump channel such that particularly is used in a positive displacement pump.

Positive displacement pumps, in which peristaltic pumps form a subclass, are employed for pumping problematic substances in particular, such as abrasive, corrosive, slurried or high-viscosity liquids and liquid-suspended solids. Peristaltic pumps are also preferred when pumping as a primary function must be complemented with accurate metering, high hygienic standard and leakproofness. Peristaltic pumps are used widely, e.g., in the manufacture of foodstuffs, drugs, oil and chemical products. In heavy industries, peristaltic pumps serve to pump, i.a., such materials as liquids and ore/mineral suspensions.

To operate properly, a peristaltic pump must be capable of forcing a volume of a fluid medium to move along a hose/tube by way of peristaltically compressing the hose from end to end during one turn of the pump rotor while simultaneously the next fluid volume is already filling the hose. Conventionally, this pumping sequence is implemented by rotating a nonrotary shoe or pressing roller, whereby the hose is subjected to progressive compression in the nip between the shoe/roller and the peripheral wall of the pump head. Furthermore, the hose/tube/tubing is selected to be sufficiently elastic and reinforces such that the hose resumes its circular profile immediately after the compression thereby creating a vacuum in its lumen thus inducing the entry of the next volume of the fluid medium into the hose.

Most generally, this pump construction is implemented by way of flexing a straight hose/tube into a semicircle adapted into the pump head cavity wherein the hose is compressed radially by two diametrically opposite shoes or rollers. This kind of pump embodiment is characterized in that the shoe or roller applies a compressive force against the hose at all times and that the pump is typically half filled with a lubricant (e.g., glycerin) serving both to transfer frictional heat to the pump's external housing structures and therefrom out from the pump as well as to reduce sliding or rolling friction occurring in the compression of the hose. However, at higher rotor speeds or operation against a high head, the pump heats up so much that it must be stopped at regular intervals for cooling down. If the pump is specified for continuous operation, the pump as well as the drive motor/gear must be overdimensioned resulting in substantial investment and operating costs. Additional costs are also incurred during service and adjustment of the pump inasmuch as the lubricant must be drained and replaced at the same time as the seals of the pump housing and shaft are replaced.

Moreover, in this kind of prior art construction, both ones of the rotor shoes/rollers begin to compress the hose at its suction end thus imparting a transient force impulse on both the stationary hose fixture and the hose itself. Such an impulse occurring twice during a single turn of the pump rotor imposes strong stresses on the hose and particularly the captive fittings of the hose ends.

In some pump constructions, attempts have been made to reduce the high abrasive friction and rapid pulsation by way of using compressing wheel rollingly running in bearings along an orbital trajectory. Herein, the hose may be bent into a full circle or even more, whereby the hose suction and discharge ends overlap. This kind of a single-contact rolling wheel minimizes the friction between the compressing wheel and the hose thus needing substantially less lubrication. Moreover, the single-contact pump rotor running over a full circle of the hose halves the number of pumping pulses, that is, only one fluid pulse instead of two is ejected from the pump per one turn of the rotor. Fluid pulsation also remains less aggressive due to the larger compressive area of the rotor that closes the lumen of the hose at a respectively slower speed resulting in slower onset/fall of the fluid pulse than in double-contact pumps. This kind of construction also has less friction and, hence, generates less heat thus facilitating continuous operation at a higher rotor speed, whereby the desired volumetric flow rate can be produced with a smaller pump, gear train and motor.

However, continuous operation at a high speed is strenuous to both the hose and, in particular, the captive fittings of the hose ends. Hence, a typical problem in prior-art positive displacement pumps of the peristaltic type is associated with the captive securing of the hose ends to the pump housing. The hose is conventionally fixed with hose clamps/inserts to a support flange mounted to the external side of the pump housing. The captive securing of the hose ends must take the line pressure imposed on the pump, seal the hose feedthrough opening so that the medium serving as hose lubricant in the pump does not leak out from the pump housing and, simultaneously, fix the hose to the pump housing so tightly that the forces imposed by the rotor on the hose cannot pull/push the hose end free.

The state of the art is represented, e.g., by patent publication FR-1114877 disclosing a construction in which a roll is adapted orbitally rotatable in the pump cavity by means of a crankshaft. The pump structure is illustrated in FIG. 2 of cited reference publication. It must be noted that the elastic pump flow channel does not cover a full 360° circle in the pump cavity.

In patent publication ZA19971675, "Orbital peristaltic pump with dynamic pump tube," is disclosed an oscillatory compressive ring adapted rotatable in the pump cavity by alternative drive means. The tube is passed a full 360° circle along the inner periphery of the pump cavity and the suction/discharge ends of the tube enter/leave the pump cavity in a tangential fashion relative to the pump housing. The cross section of the tube is shown in FIG. 6 of cited reference publication.

A crucial problem hampering prior-art constructions is the total lack of an adjustment mechanism for setting the compressive force. More specifically, no facility is provided for setting the compression applied on the pump hose or like elastic flow channel, whereby the distance between the rotor and the pump cavity cannot be varied from a constant value. In addition to the shortcomings listed above, conventional embodiments of the captive fitting of the hose to the pump housing are often implemented in an extremely awkward fashion. In other words, the technical implementation in regard to its practicable functionality and everyday servicing has mostly been neglected entirely.

Almost invariably, the above-mentioned problems are associated with each other and often in an intimate causal relation to each other. Hence, it appears to be extremely essential for efficient and service-friendly operation of a peristaltic pump that further attempts are made to develop a system featuring simple and reliable captive fitting of the hose as well as an adjustment mechanism of the hose compression.

It is an object of the present invention to overcome the above disadvantages. The goal of the invention is attained by means of a combination assembly for managing a hose or like elastic pump tube or pump channel, in particular such a hose/tube that is used in a positive displacement pump.

The specifications of an assembly according to the invention are disclosed in the characterizing parts of appended claims. The invention differs from the prior art by virtue of having the pump equipped with an assembly suited for the adjustment of the pump pressure and/or compression imposed on the hose/tube, the assembly featuring a mechanism with steplessly adjustable eccentricity. In addition to this feature, the invention is characterized in that the peristaltic pump is adaptable to use, either alone or in conjunction with the eccentric adjustment mechanism, a captive hose fitting system for managing the pressure imposed on the pump hose/tube.

In the following, the invention is described in more detail by making reference to the appended drawings in which FIG. 1 is an illustration of an embodiment of a peristaltic hose pump;

Figure 1:
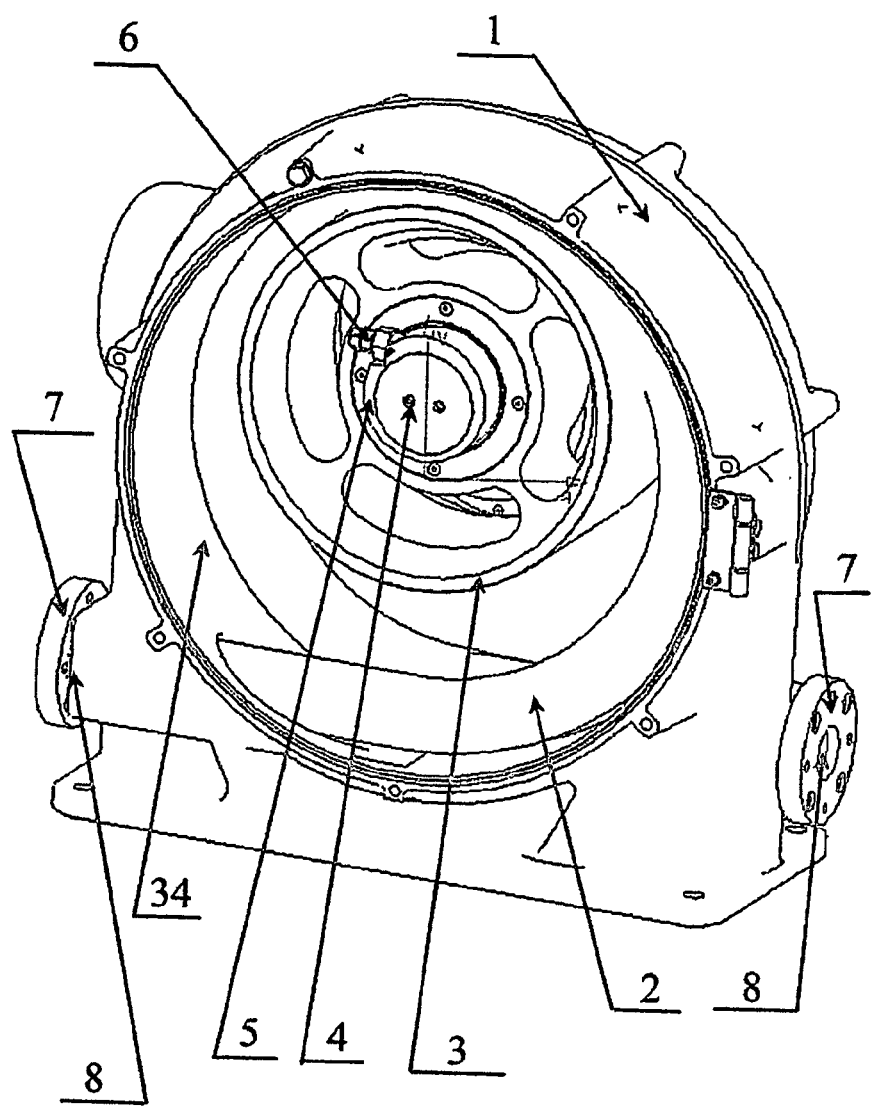

Referring to FIG. 1, therein are shown the main components of a peristaltic pump. The pump comprises a pump body 1, a hose 2 and a rotor 3 mounted freely rotatable on bearings mounted onto an eccentric adjustment bushing 5. The eccentric adjustment bushing in turn is mounted on a crankshaft pin denoted by reference numeral 10 of FIG. 2. The crankshaft is mounted on bearings on the rear wall of pump body 1, centrally in regard to the pump cavity 34. The hose or like elastic pump tube or pump channel is inserted into the pump cavity with the rotor housed therein, whereby the hose rests against the pump cavity inner perimeter so as to cover a full circle. The hose ends are captively fitted in feedthrough openings 8 of the pump body. Actuated by the drive means, the crankshaft forces the rotor to rotate in the pump cavity at a given distance from the interior perimeter of the pump cavity. This distance is set smaller than the two-fold thickness of the hose/tube wall. Hereby, the rotor compresses the hose inserted in the pump cavity so that, with the rotation of the rotor, the volume of fluid medium being pumped and contained in the hose in front of the rotor is prevented from leaking in the reverse direction past the point of the hose compressed by the rotor. With the rotation of the rotor in the pump cavity, it rolls over the hose surface thus propelling the bulk of fluid medium contained in the hose. With the rotary progressive motion of the rotor and the hose recovering its circular profile immediately after the point of rotor compression, the hose creates a vacuum that causes the hose to become refilled with the fluid medium being pumped.

Figure 2:
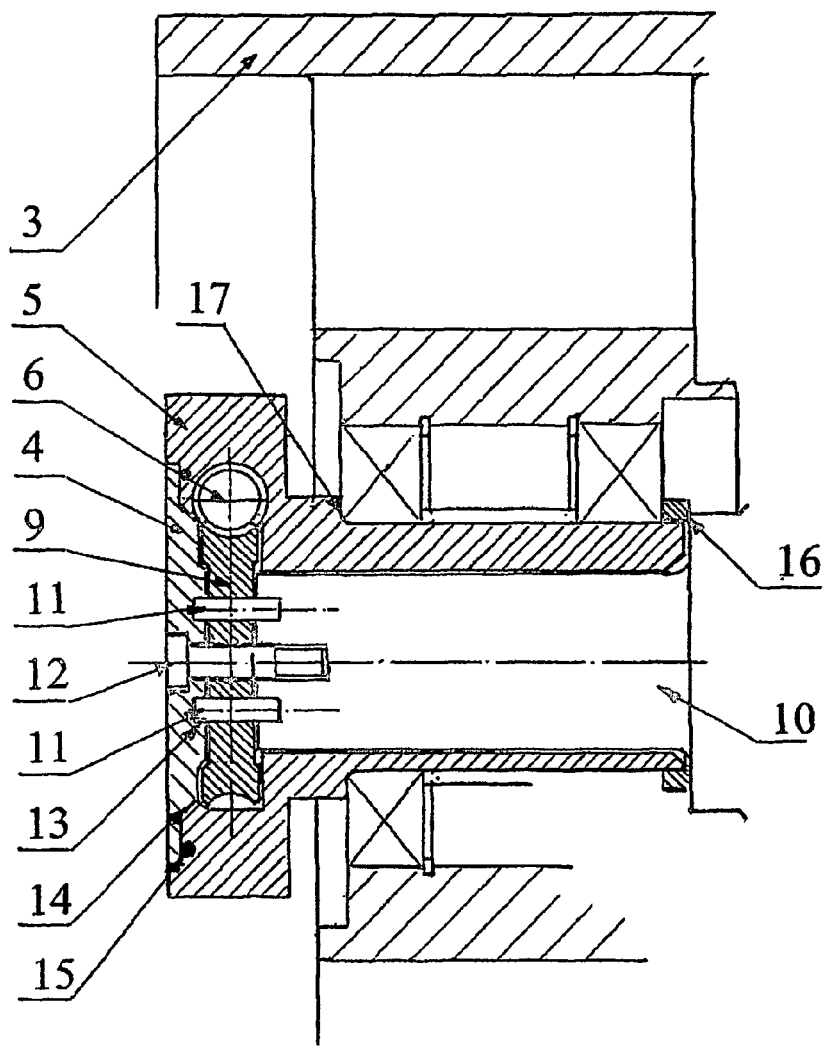
FIG. 2 is a cross-sectional side elevation view of an eccentric adjustment mechanism according to the invention adapted to a peristaltic pump.
Figure 3:
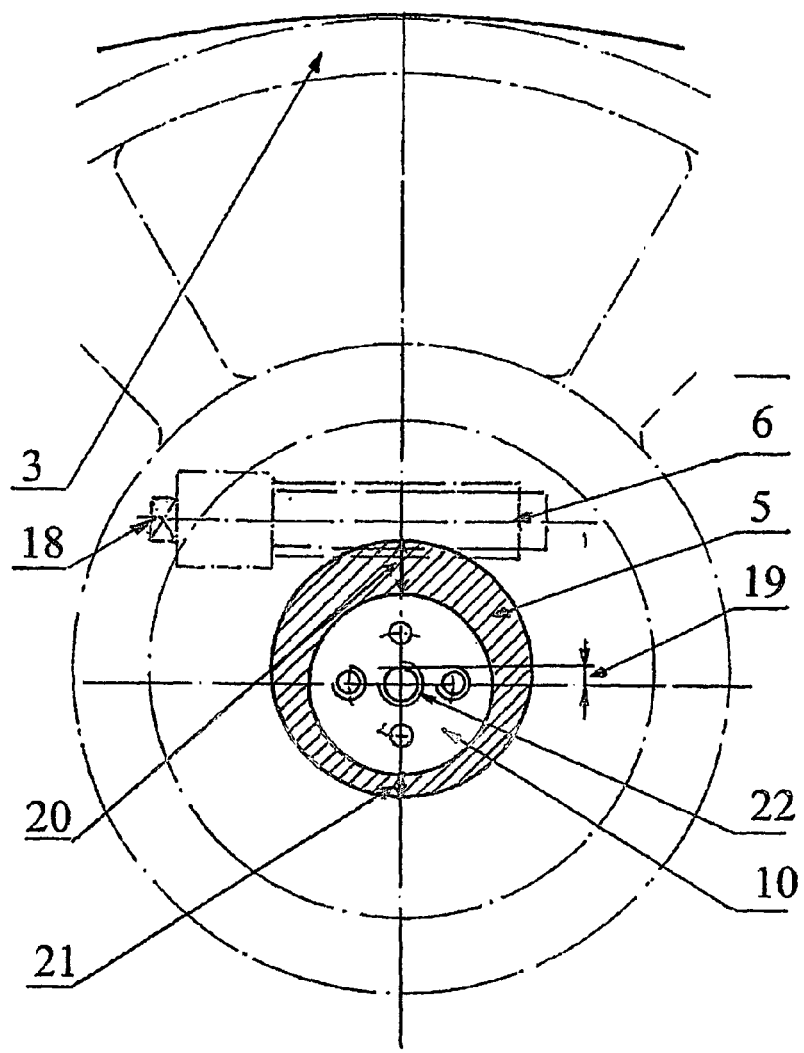
FIG. 3 is a cross-sectional front elevation view of an eccentric adjustment mechanism according to the invention set into its uppermost position.
Figure 4:
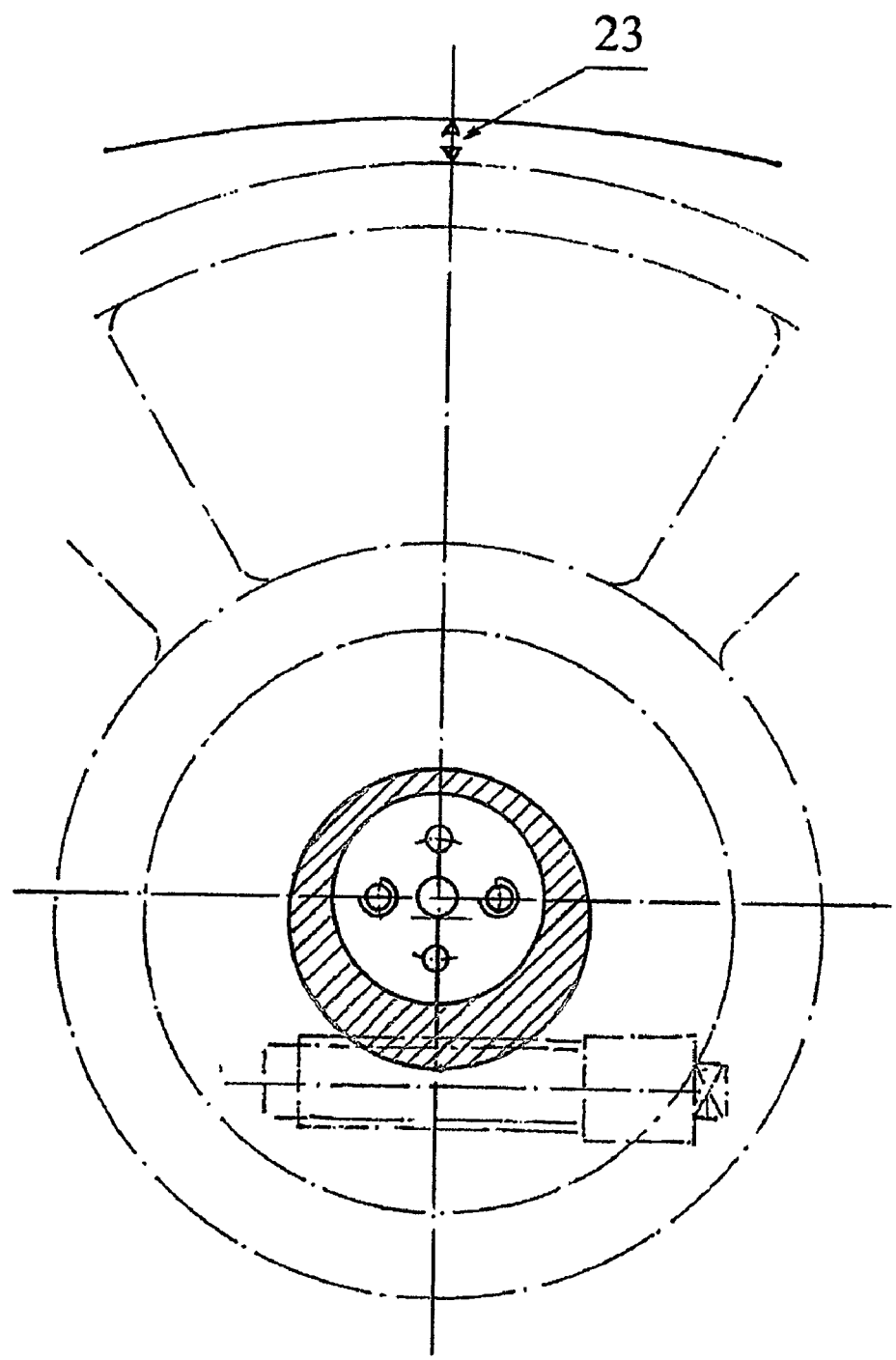
FIG. 4 is a cross-sectional front elevation view of an eccentric adjustment mechanism according to the invention set into its lowermost position.

In FIGS. 2, 3 and 4 is shown an eccentric adjustment mechanism comprising an eccentric adjustment bushing 5, a worm gear 6, a spur gear 9, a lockcover 4, lockpins 11 and locking bolt(s) 12. The eccentric adjustment mechanism serves to adjust the gap 23 shown in FIG. 4 between the rotor outer surface and the pump cavity inner periphery that determines the compressive force imposed on the hose. The rotor gap is adjusted by rotation of the eccentric bushing 5 mounted on the crankshaft pin 10. The rotor in turn is mounted on a bearing on the outer periphery of the eccentric bushing. The eccentricity 19 of the adjustment bushing illustrated in FIG. 3 is accomplished by drilling the bore of the bushing eccentrically in regard to the outer periphery of the bushing.

The rotation of the eccentric adjustment bushing takes place with the help of a reduction gear such as a worm gear adapted between the eccentric bushing and the crankshaft. The reduction gear is constructed by adapting the worm 6, i.e., the driving shaft of the reduction gear, into the solid body part of the eccentric bushing. The spur gear 9, i.e., the driven gear, is mounted to the end of the crankshaft pin. Alternatively, the driven spur gear 9 may also be machined directly to the end of the crankshaft pin. With the rotation of the driving shaft, the eccentric bushing turns on the crankshaft pin, whereby the distance 23 between the rotor outer periphery and the pump cavity inner periphery changes as shown in FIG. 4. The maximum possible span of pump rotor-to-body distance adjustment is equal to the difference between wall thicknesses 20 and 21 of bushing 5 as shown in FIG. 3.

A worm gear or like self-locking gear is advantageously used as the reduction gear. This allows the rotor gap adjustment to be carried out accurately and easily by a single operator, since the compressive force applied to the hose cannot rotate the bushing backward inasmuch as the self-locking reduction gear prevents uncontrolled rotation of the bushing. Based on the use of a toothed reduction gear, the rotor gap adjustment can be performed without the need for any special tools or adjustment shims.

In a running pump, the eccentric adjustment bushing is continually subjected to forces that tend to rotate the eccentric bushing. With the help of lockcover 4, the eccentric bushing is locked to the crankshaft pin so that the reduction gear need not take all the rotational forces directed to the eccentric bushing during the operation of the pump. The lockcover is clamped against a conical surface 14 of the eccentric bushing with a bolt 12 illustrated in FIG. 2 to pass through the lockcover and fit into a threaded hole 22 of the crankshaft end shown in FIG. 3. In addition to providing the locking force of the conical fit, the tightened bolt presses a sealing O-ring 15 placed between the lockcover flange and the eccentric bushing in order to prevent the hose lubricant or other contamination from entering into the reduction gear and the interface between the eccentric bushing and the crankshaft pin. Thus, the screws passing through the lockcover only serve to provide the clamping force that keeps the lockcover tight against the conical surface 13. The force, which tends to rotate the eccentric bushing and is transmitted via the conical interface between the lockcover and the eccentric bushing, is transmitted further to the crankshaft end via the locking between the crankshaft and the lockcover. This locking is accomplished with the help of lockpins 11 sunken in the crankshaft end or a key slot. The lockcover is respectively provided with recesses 13 mating with the lockpins or key.

By virtue of the lockcover, also the inner races of the bearings mounted on the eccentric bushing can be clamped axially between a shoulder 17 of the eccentric bushing and a shoulder 16 of the crankshaft. This is necessary to clamp the inner races of the bearings in a stationary and tight fit between the shoulders of the eccentric bushing and the crankshaft thus preventing the bearings from having a play in regard to the eccentric bushing.

A characteristic property of a peristaltic pump based on positive displacement is that the inner surface of the hose/tube erodes during pumping. This process reduces the hose wall thickness and, thence, the compression of the hose in the gap between the pump rotor and body. Hence, the hose compression must be adjusted during the life of the hose. During continuous use, the known wall thickness of the hose wears down to an unknown value. In such a situation, it is very difficult to establish valid rules to be applied in conventional techniques of correct adjustment of hose compression. Invalid adjustment rules must be complemented with practical operating experience that frequently invokes serious overcompression and pump damage situations. In contrast, the eccentric adjustment assembly disclosed in the present application allows runtime adjustment of hose compression to be carried out simply with a calibrated torque wrench. The end 18 of the worm is so shaped as to be rotatable by means of the torque wrench. As the worm is thus turned with the torque wrench, an accurately set torque can be applied during rotation of the worm. With the applied torque thus being always constant, also the compressive force imposed on the hose becomes sufficiently accurately set to a constant value. In the adjustment of hose compression, it is important to apply a constant tightening torque at all times in order to compensate for slackening compression due to the wear of the hose.

In FIG. 3 the eccentric adjustment is shown set into its minimum compression gap position. In FIG. 4 respectively, the eccentric adjustment is shown set into a position wherein the compression gap 23 is set to its maximum value.

Figure 5:
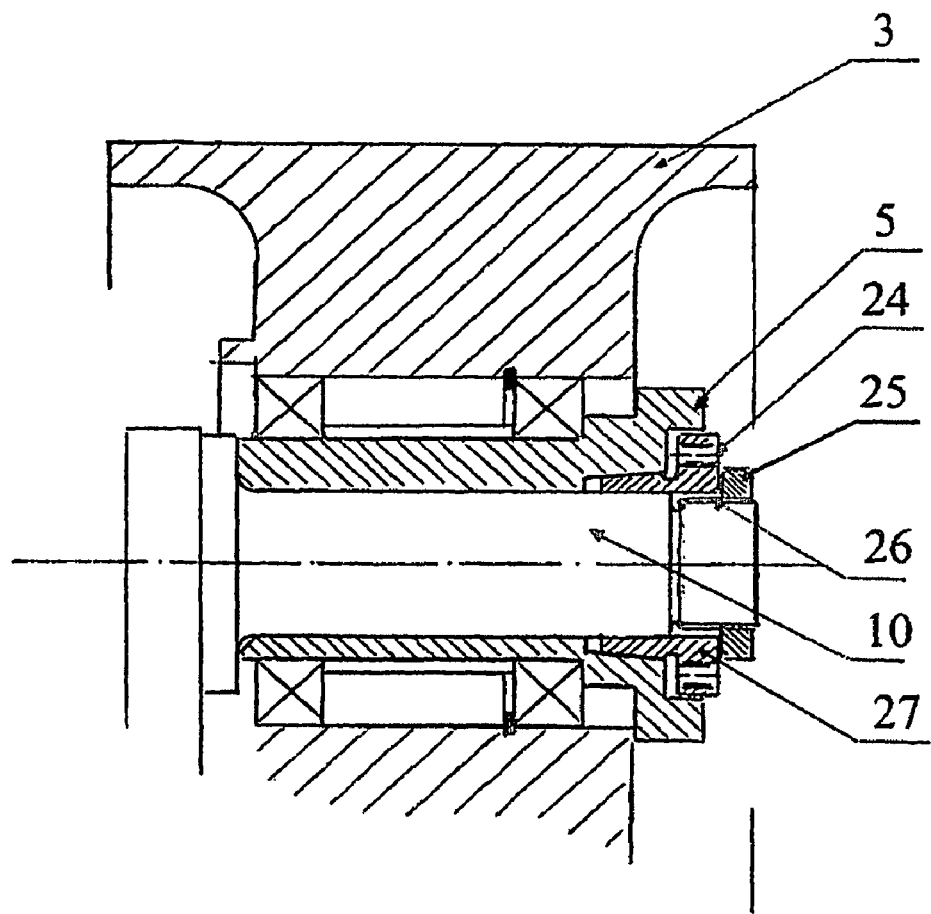
FIG. 5 is a cross-sectional view of an eccentric adjustment mechanism according to the invention.

In FIG. 5 is shown an alternative embodiment of the eccentric adjustment assembly according to the invention. This modification of the adjustment assembly is suited for setting the hose compression particularly in small-size pumps in which the adoption of the above-described reduction-gear-based adjustment arrangement is not economically or physically viable.

The eccentric adjustment assembly of FIG. 5 comprises a locknut 25 at the crankshaft end, a lockcone 27 and an eccentric bushing 5. In this embodiment, the hose compression adjustment is based on the same eccentric adjustment concept as described above and illustrated in FIG. 2. The principal differences between these two embodiments are seen in the technique of providing the torque for rotating the cone bushing and in the arrangement for locking the eccentric bushing in place. Rotation of the eccentric bushing on the crankshaft pin takes place by turning the bushing by the keyhead of its flange with a conventional wrench or tongs. The eccentric bushing is locked into the desired adjustment position by the lockcone 27. The lockcone is pressed home by way of tightening the locknut 25 onto an outer thread 26 made on the crankshaft end. The locknut is secured to the shaft with a tab washer. The lockcone is detached with the help of extractor threads 24 made on the flange of the lockcone. To this end, the lockcone flange is provided with two threaded holes 24 wherein extractor bolts can be fifted to remove the lockcone. The bolts are tightened until their tips meet an inner shoulder of the eccentric bushing, whereby they force the eccentric bushing off from its place. For precise hose compression adjustment, between the tab wafer and the eccentric bushing may be placed a dial plate with a graduation needed in the adjustment. The dial plate is secured to the shaft with the help of the same key slot as is used for securing the tab washer.

Figure 6:
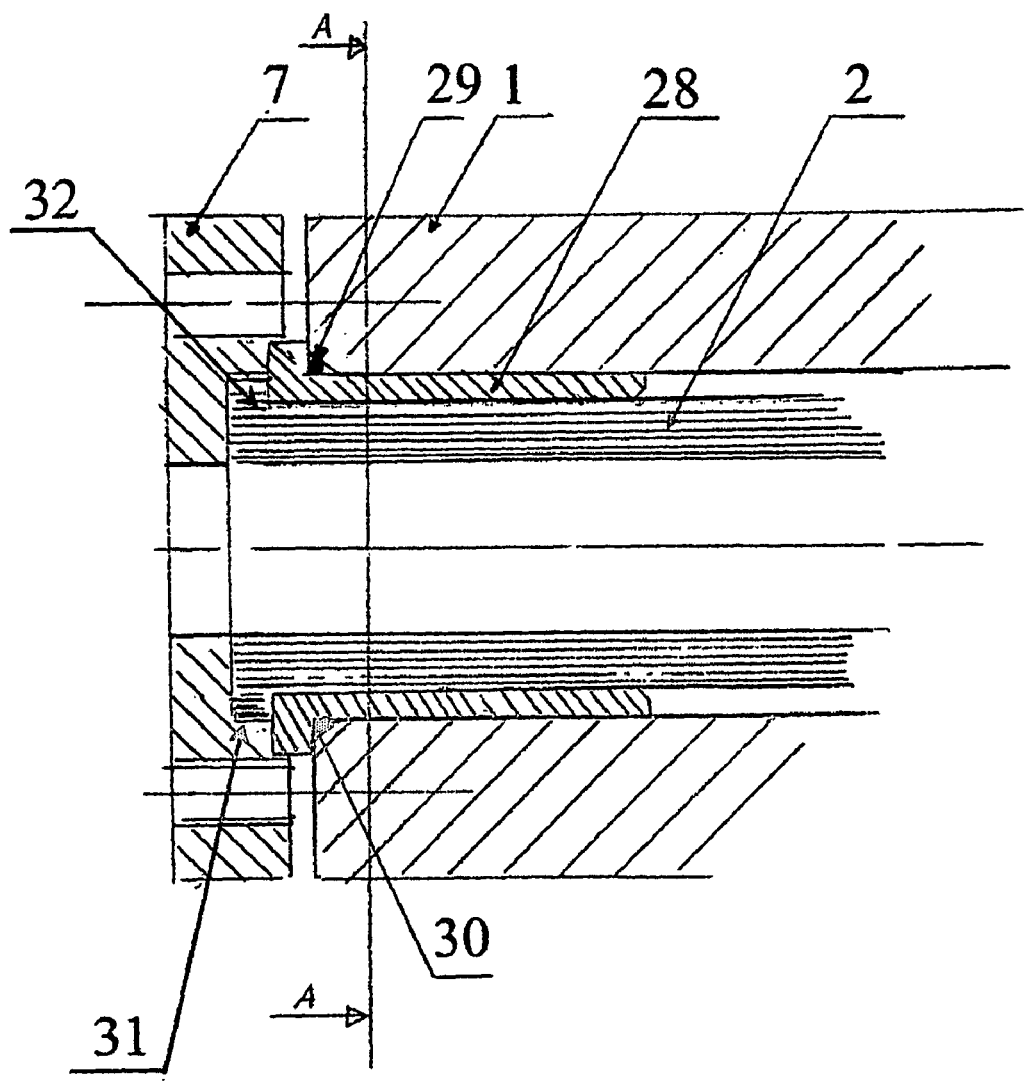
FIG. 6 is a longitudinally sectional view of a captive hose fitting system according to the invention adapted to a peristaltic pump.
Figure 7:
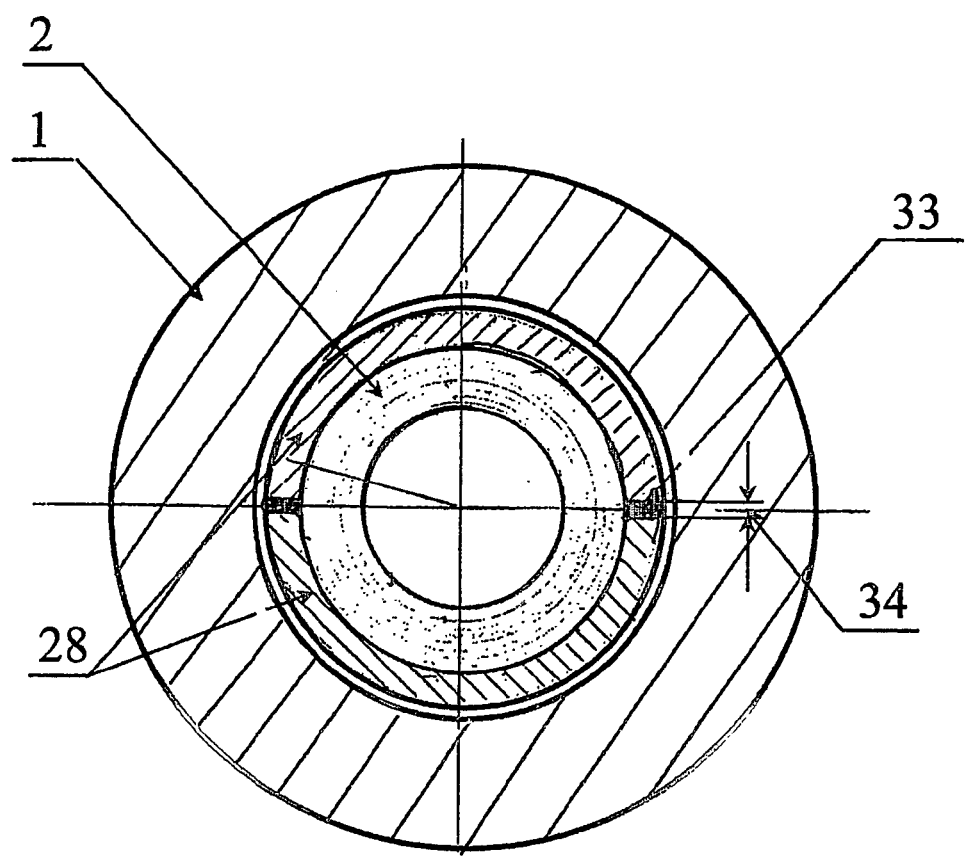
FIG. 7 is a cross-sectional view of a captive hose fitting system according to the invention adapted to a peristaltic pump.
Figure 8:
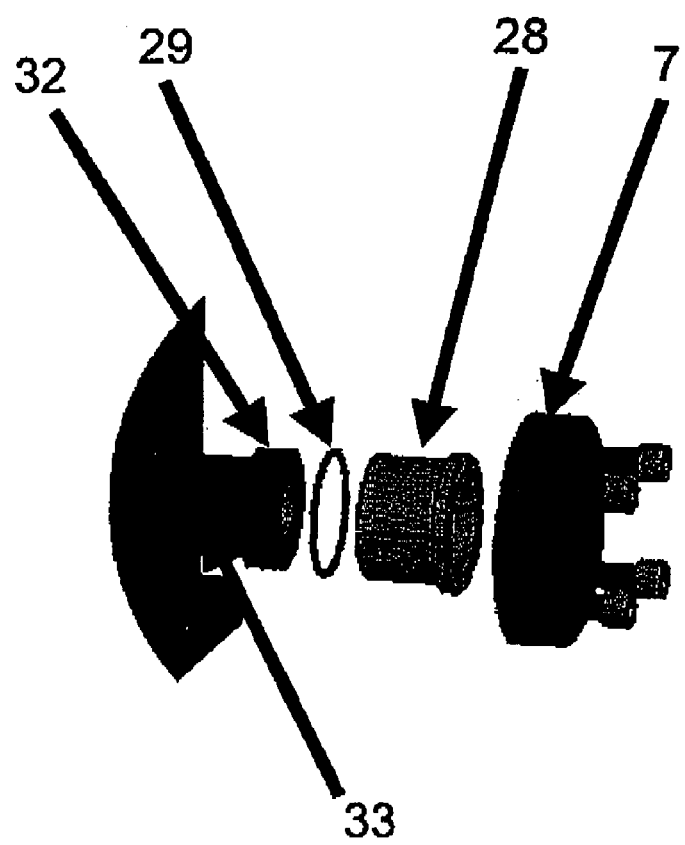
FIG. 8 is an exploded view of a captive hose fitting system according to the invention adapted to a peristaltic pump.

A captive hose fitting system complementing the assembly according to the invention is shown in FIGS. 6, 7 and 8. The captive system comprises a rubber flange 32 inserted to the hose end, seal gills advantageously comprising two gills 33, and two halves of a split collet 28 and a mounting flange 7 that may be replaced by a conventional piping flange if so desired.

The seal gills 33 project from the hose end in a form with the diametrical dimension across the outer edges of the seal gills matching the outer diameter of the hose end flange. The seal gills are situated about the outer perimeter of the hose, at opposite sides thereof relative to each other. The cross section of the seal gills is made 0.5 to 1 mm thicker than the width of the slits 34 made to the collet as it is divided into two halves.

The feedthrough opening in the pump body is of the same size or slightly larger than the outer diameter of the hose end flange 32 formed on the hose end. To mount the hose into the pump cavity, the hose end is passed from inside the cavity outward via the feedthrough opening. The length of the tree hose end projecting out from the feedthrough opening is trimmed to about twice the hose thickness. The split collet 28 is placed about the hose end, behind the hose end flange 32, so that the seal gills 33 remain trapped between the split collet halves. Next, the flange of the split collet is fitted against the hose end flange already formed on the hose end. To the rear side of the flange of the split collet is placed an O-ring 29. Finally, the hose end is pushed back into the pump cavity so deep that the flange of the split collet remains resting against the pump body 1. Then, the O-ring placed on the split collet remains compressed in the gap between the flange of the split collet and a bevel 30 made to the edge of the feedthrough opening of the pump body thus exerting a force that presses the halves of the split collet against the seal gills. Resultingly, a seal is established between the perimeter of the split collet and the pump cavity. The captive fitting set comprising the hose end flange, the split collet and the O-ring is tightened with the help of mounting screws 7 against the rim of the feedthrough opening made on the pump body. To accommodate the hose end flange, the mounting flange has a sunken shoulder 31 made thereon serving to prevent overtightening of the hose end flange. The depth of the sunken shoulder is dimensioned such that the mounting flange meets the flange of the split collet at a depth where the compression off the hose end flange at the hose end is about 30%. This amount of compression is sufficient to keep the hose end firmly clamped. Excessive compression of the hose end flange damages the hose end flange thus impairing the strength of the flange. In certain cases, the fixing holes of the mounting flange can be drilled into the same positions as those of a standardized piping flange corresponding to the nominal size and pressure specifications of the pump. Then, the mounting flange can be replaced by a conventional piping flange if so desired.

A steel ring embedded in the hose end flange further assures that the hose end flange retains its shape and the flange cannot slip off from its captive position even under heavy mechanical stress. The seal gills, which provide the sealing of the longitudinal gaps between the halves of the slit collet employed in the clamping of the pump hose, also serve as indicators during the mounting of the pump hose to verify that the pump hose is clamped straight, not in a twisted position. The seal gills are cast such that they are in a horizontal position when the pump hose is correctly mounted.

To a person skilled in the art it is obvious that the invention is not limited by the above-described exemplifying embodiment, but rather may be varied within the inventive spirit and scope of the appended claims. In addition to those described above, more benefits are obtained by virtue of the constructions implemented in the assembly of the invention. The captive hose fitting system provides simple and pull-resistant securing of the pump hose. The arrangement disclosed herein permits the use of a flanged hose and sealed feedthrough of the hose. The hose fitting system also facilitates correct and easy mounting of the hose and verification of the mounting. Additionally, it allows the use of a standardized piping flange to be used for pump connections.

Respectively, the benefits and inventiveness of the eccentric adjustment assembly are appreciated, i.a., in reliable and accurate setting of hose compression force also on a worn hose. The eccentric adjustment bushing assembly the bearing to be tightened lashless onto the eccentric bushing with the help of the lockcover and, further, locking of the eccentric bushing and sealing of the compression adjustment gear with the help of the lockcover. All the adjustments can be carried out by a single operator without the need for special tools and storage of multiple spare parts separately.

The assembly according to the invention represents a substantial advancement in the construction of a peristaltic pump as to its efficiency, operational reliability and, in particular, ease of service. The invention is characterized in that the assembly disclosed herein relates to the pumping of liquids and slurries by way of progressively compressing an elastic hose, starting from the hose suction end and finishing at the hose discharge end, whereby the progressive compression transfers forward the liquid or slurry volume in front of the compression point. Both of the mechanical constructions described above are advantageously utilized in the assembly according to the invention. The object of the invention is particularly directed to a novel and inventive approach to inserting the pump hose into the pump cavity, a captive fixing system for the hose ends, a replacement method of the hose giving minimized downtime, and an adjustment/locking mechanism of the compression applied to the hose.

What is claimed is:

1. A combination assembly for managing a pump hose or elastic pump tube or pump channel used in a peristaltic pump, wherein the pump comprises a rotor (3) that compresses the hose/tube and an assembly that adjusts the pump pressure and/or compression imposed on the hose/tube, the assembly comprising a steplessly adjustable eccentric adjustment mechanism which cooperates with the rotor to directly control the compressive force imposed on the hose/tube, the eccentric adjustment mechanism comprising an eccentric adjustment bushing (5) mounted on a crankshaft pin (10), a worm gear (6) having an end (18) dimensioned and configured to be rotated by means of a calibrated torque wrench, wherein said worm gear is mounted inside the eccentric adjustment bushing, a spur gear (9), a lockcover (4), lockpins (11) and at least one locking bolt (12), wherein a fixed torque is applied to the worm gear (6) using the calibrated torque wrench that rotates the worm gear (6) and the eccentric adjustment bushing (5) mounted on the crankshaft pin (10) whereby the gap (23) between the rotor outer surface and a pump cavity inner periphery is changed and a constant compressive force is imposed on the hose/tube.

2. The combination assembly of claim 1, characterized in that the eccentricity (is) of the eccentric adjustment bushing is accomplished by drilling the bore of the bushing eccentrically in regard to the outer periphery of the bushing.

3. The combination assembly of claim 2, characterized in that the rotation of the eccentric adjustment bushing is accomplished by means of a reduction gear adapted between the eccentric adjustment bushing and the crankshaft.

4. The combination assembly of claim 1, characterized in that a spur gear (9) is mounted to the end of the crankshaft pin or, alternatively, is machined directly to the end of the crankshaft pin.

5. The combination assembly of claim 1, characterized in that the eccentric adjustment bushing is locked to the crankshaft pin with the help of the lockcover (4) that is clamped against a conical surface (14) of the eccentric adjustment bushing with a bolt (12), whereby simultaneously, the force imposed by the tightened bolt presses a sealing O-ring (15) placed between the lockcover flange and the eccentric adjustment bushing.

6. The combination assembly of claim 1, characterized in that the rotation of the lockcover is prevented with the help of the lockpins (ii) placed between the crankshaft pin end and the lockcover.

7. The combination assembly of claim 1, characterized in that, by virtue of the lockcover, the inner races of the bearings mounted on the eccentric adjustment bushing are clamped axially between a shoulder (17) of the eccentric adjustment bushing and a shoulder (is) of the crankshaft.

8. The combination assembly of claim 1, characterized in that the peristaltic pump is adaptable to employ, either alone or in conjunction with the eccentric adjustment mechanism, a captive hose fitting system for managing the pressure imposed on the pump hose/tube.

9. The combination assembly of claim 8, characterized in that the captive hose fitting system comprises a rubber flange (32) formed on the hose end, seal gills advantageously comprising two gills (33), and two halves of a split collet (28) and, optionally, a mounting flange (7).

10. The combination assembly of claim 9, characterized in that the seal gills (33) are made to project radially outwardly from the hone end in a form with the diametrical dimension across the outer edges of the seal gills matching the outer diameter of the hose end flange, and the seal gills being situated about the outer perimeter of the hose, at opposite sides thereof relative to each other, whereby the cross section of the seal gills is made 0.5 to 1 mm thicker than the width of the slits (34) made to the collet as it is divided into two halves.

11. The combination assembly of claim 9, characterized in that the feedthrough opening made on the pump body is of the same size or slightly larger than the outer diameter of the hose end flange (32) formed on the hose end and that the split collet is placed about the hose end flange, behind the hose end flange (32) so that the seal gills remain trapped between the split collet halves.

12. The combination assembly of claim 9, characterized in that the flange of the split collet is fitted against the hose end flange formed on the hose end, and that to the rear side of the flange of the split collet is placed an O-ring (29), which becomes compressed in the gap between the flange of the split collet and a bevel (30) made to the edge of the feedthrough opening of the pump body thus exerting a force that presses the halves of the split collet against the seal gills and seals the gap between the split collet and the pump body.

13. The combination assembly of claim 9, characterized in that to the mounting flange is made a sunken shoulder (31) serving to prevent overtightening of the hose end flange.

* * * * *